(12) United States Patent
Ho

(10) Patent No.: US 8,171,934 B1
(45) Date of Patent: May 8, 2012

(54) FOREHEAD PAD AND FOREHEAD SUPPORT ASSEMBLY

(75) Inventor: Peter Chi Fai Ho, Pittsburgh, PA (US)

(73) Assignee: RIC Investments, LLC, Wilmington, DE (US)

( * ) Notice: Subject to any disclaimer, the term of this patent is extended or adjusted under 35 U.S.C. 154(b) by 1258 days.

(21) Appl. No.: 11/485,767

(22) Filed: Jul. 13, 2006

Related U.S. Application Data

(60) Provisional application No. 60/699,784, filed on Jul. 15, 2005.

(51) Int. Cl.
*A62B 18/08* (2006.01)
(52) U.S. Cl. .......... 128/207.11; 128/206.21; 128/206.24
(58) Field of Classification Search ............. 128/207.11, 128/206.21, 206.23–28, 205.25
See application file for complete search history.

(56) References Cited

U.S. PATENT DOCUMENTS

| | | | |
|---|---|---|---|
| 3,362,403 A | 1/1968 | Fleming et al. | |
| 3,622,233 A | 11/1971 | Blood et al. | |
| 4,907,584 A | 3/1990 | McGinnis | |
| 5,243,971 A | 9/1993 | Sullivan et al. | |
| 5,517,986 A | 5/1996 | Starr et al. | |
| 5,570,689 A | 11/1996 | Starr et al. | |
| 6,119,693 A | 9/2000 | Kowk et al. | |
| D439,326 S | 3/2001 | Hecker et al. | |
| 6,357,441 B1 | 3/2002 | Kowk et al. | |
| 6,463,931 B1 | 10/2002 | Kwok et al. | |
| 6,467,483 B1 | 10/2002 | Kopacko | |
| 6,520,182 B1 | 2/2003 | Gunaratnam | |
| 6,532,961 B1 | 3/2003 | Kwok et al. | |
| 6,557,556 B2 | 5/2003 | Kwok et al. | |
| 6,679,261 B2 | 1/2004 | Lithgow et al. | |
| 2003/0019496 A1* | 1/2003 | Kopacko et al. | 128/206.24 |
| 2004/0045551 A1* | 3/2004 | Eaton et al. | 128/206.21 |
| 2004/0112387 A1 | 6/2004 | Lang et al. | |
| 2005/0005940 A1* | 1/2005 | Gunaratnam | 128/206.27 |
| 2005/0011522 A1* | 1/2005 | Ho et al. | 128/206.21 |
| 2005/0022820 A1 | 2/2005 | Kwok et al. | |

FOREIGN PATENT DOCUMENTS

| | | | |
|---|---|---|---|
| EP | 1205205 A2 * | 5/2002 | |
| WO | WO 2005009521 A1 * | 2/2005 | |

OTHER PUBLICATIONS

MAP Medizin-Technologie GmbH, Papillon® Instruction Manual, 2002.
MAP Medizin-Technologie GmbH, Papillon® Instruction Manual.
Respironics, Inc., ComfortClassic™, 2001.

* cited by examiner

*Primary Examiner* — Justine Yu
*Assistant Examiner* — Colin W Stuart
(74) *Attorney, Agent, or Firm* — Michael W. Haas

(57) ABSTRACT

A forehead pad including a coupling portion for attachment to a forehead support member, and a contact portion for contacting a patient's forehead. The contact portion includes a contact portion shell formed as an outer wall, which defines a single, continuous inner cavity. The contact portion shell is formed from a substantially deformable material, such that the wall of the contact portion shell is deformable and deflectable upon contact with the patient's forehead. The continuous inner cavity does not include any support structure positioned within the cavity. A forehead support assembly is also disclosed.

17 Claims, 9 Drawing Sheets

FOREHEAD PAD AND FOREHEAD SUPPORT ASSEMBLY

CROSS-REFERENCE TO RELATED APPLICATIONS

This application claims priority under 35 U.S.C. §119(e) from provisional U.S. patent application No. 60/699,784 filed Jul. 15, 2005 the contents of which are incorporated herein by reference.

BACKGROUND OF THE INVENTION

1. Field of the Invention

The present invention relates generally to structures and assemblies for use in connection with a patient interface device, and, in particular, to a forehead pad and forehead support assembly for use in connection with a patient interface device that provides additional comfort to the patient.

2. Description of the Related Art

There are numerous situations where it is necessary or desirable to deliver a flow of breathing gas, non-invasively, to the airway of a patient, i.e., without intubating the patient or surgically inserting a tracheotomy tube in their trachea. For example, it is known to ventilate a patient using a technique known as non-invasive ventilation (NIV). It is also known to deliver continuous positive airway pressure (CPAP) or variable airway pressure, which varies with the patient's respiratory cycle or a monitored condition of the patient, to treat a medical disorder, such as sleep apnea syndrome, in particular, obstructive sleep apnea (OSA), congestive heart failure, stroke, Cheynes-Stokes respiration, etc. Non-invasive ventilation and pressure support therapies involve the placement of a patient interface device, which is typically a nasal or nasal/oral mask, on the face of a patient to interface the ventilator or pressure support device with the airway of the patient, so that a flow of breathing gas can be delivered from the pressure/flow generating device to the airway of the patient.

Patients suffering from a pulmonary or respiratory disorder, such as obstructive sleep apnea, are often treated with a pressure support device, such as a CPAP device. A CPAP device delivers a flow of fluid to the airway of the patient throughout the patient's breathing cycle in order to "splint" the airway, thereby preventing its collapse during sleep. In another type of treatment, bi-level positive pressure therapy is provided to the patient, in which the pressure of air delivered to the patient's airway varies or is synchronized with the patient's breathing cycle to maximize therapeutic effect and comfort to the patient. A pressure support device may also provide "bi-level" pressure support, in which a lower pressure is delivered to that patient during the patient's expiratory phase then during the inspiratory phase.

It is also known to provide an auto-titration positive pressure therapy in which the pressure provided to the patient changes based upon the detected conditions of the patient, such as whether the patient is snoring or experiencing an apnea, hypopnea, or upper airway resistance. Such a device adjusts the pressure delivered to the patient, based on whether or not the patient is snoring. For example, a pressure support device may actively test the patient's airway to determine whether obstruction, complete or partial, could occur and adjust the pressure output to avoid this result.

Other modes of providing positive pressure support to a patient are known. For example, a proportional assist ventilation mode of pressure support provides a positive pressure therapy in which the pressure of gas delivered to the patient varies with the patient's breathing effort to increase the comfort of the patient. Proportional positive airway pressure (PPAP) devices deliver breathing gas to the patient based on the flow generated by the patient.

For purposes of the present invention, the phrase "pressure support system", "pressure support device", or "positive pressure support" includes any medical device or method that delivers a flow of breathing gas to the airway of a patient, including a ventilator, CPAP, bi-level, PAV, PPAP, or bi-level pressure support system.

Because such patient interface devices are typically worn for an extended period of time, a variety of concerns must be taken into consideration. For example, in providing CPAP or other positive pressure therapy to treat OSA, the patient normally wears the patient interface device all night long while he or she sleeps. One concern in such a situation is that the patient interface device is as comfortable as possible, otherwise the patient may avoid wearing the interface device, defeating the purpose of the prescribed pressure support therapy.

In order to provide gas or, as discussed above, oxygen, to a patient, the patient must use a patient interface device, such as a respiratory mask, as known in the art. These respiratory masks are provided in many variations, such as nasal masks, nasal and oral masks, mouth masks, full-face masks, etc. All of these mask devices are used to provide oxygen or air to the patient. Typically, the gas stream is extracted from a pressure generating device, such as those devices discussed above, which may be, in turn, in fluid communication with an oxygen tank. The oxygen flows from the source through the regulator devices, through the pressure generating device and further through a conduit into the mask. The pressure generating device and the conduit, such as a gas hose, are considered the patient circuit, such that a coupling assembly is required for connecting the patient circuit to the patient interface device.

In a conventional pressure support system, a flexible conduit is coupled to an exit conduit. The flexible conduit forms part of the patient circuit that carries the flow of breathing gas from the pressure generating system to the patient interface device. In a support system, the patient interface device connects the patient circuit with the airway of the patient so that the elevated pressure gas flow is delivered to the patient's airway. Examples of patient interface devices include a nasal mask, nasal and oral mask, full-face mask, nasal cannula, oral mouthpiece, tracheal tube, endotracheal tube, or hood.

It is known in the art to provide forehead support assemblies associated with gas delivery masks to provide a support mechanism between the mask and the patient's forehead. Gas delivery masks having forehead cushions, spacers or supports are described in U.S. Pat. Nos. 4,907,584; 5,243,971; 5,570,689; 6,119,693; 6,357,441; 6,463,931; 6,467,483; 6,520,182; 6,532,961; and 6,557,556. The forehead support assemblies and associated structures and members serve to prevent the mask from exerting additional and unrequired force on a patient's face, and further provide stability to the mask when attached to the patient.

For example, in U.S. Pat. No. 6,557,556 ("the '556 patent") discloses a forehead support for facial mask that includes multiple pads that provide the contact points on the user for the forehead support. In addition, these pads include an inner cavity of annular interior with two retaining walls. These retaining walls provide structural integrity to the pads, and limit deformation of these pads.

The forehead support assemblies disclosed in the above-referenced patents typically have at least one forehead pad attached to the forehead support member. The forehead pad contacts the surface of the forehead of the patient. In U.S. Pat. Nos. 4,907,584; 5,243,971; 5,517,986; 5,570,689; and 6,357, 441, the forehead support pads are typically formed from a foam material and generally have a rectangular or trapezoidal shape with relatively sharp edges. The conventional forehead pads taught in U.S. Pat. Nos. 6,119,693; 6,463,931; 6,467,483; 6,520,182; 6,532,961; and 6,557,556 have a semi-circular profile to compensate for any angular variation between the forehead support assembly structure and the surface of the patient's forehead. The disadvantage of such a design is that the forehead pad rests on the forehead on a curved surface, which translates into an undesirable pressure point. These semi-circular designs allow the curved contact to compress and deform to secure a flatter contact area. However, this also creates pressure points and illustrates a less comfortable option.

The product literature for the MAP Papillon mask discloses a forehead pad that attaches to the forehead support member via a stem. The stem and/or the attachment of the stem to the forehead support frame allow for some articulation of the main portion of the forehead pad. However, the relatively small size of the stem provides a relatively unstable platform for mounting the forehead pad on the support frame or forehead support member.

SUMMARY OF THE INVENTION

Accordingly, it is an object of the present invention to provide a forehead pad and forehead support assembly that addresses the above-identified concerns and overcomes the shortcomings of conventional forehead support assemblies in the gas delivery art. It is another object of the present invention to provide a forehead pad and forehead support assembly that represents a much more comfortable option to the patient when attaching the patient interface device. It is a further object of the present invention to provide a forehead pad and a forehead support assembly that reduces and/or eliminates the pressure points associated with conventional forehead pads and forehead support assemblies.

Accordingly, the present invention is directed to a forehead pad for use in connection with a forehead support assembly having a forehead support member. The forehead pad includes a coupling portion and a contact portion. The contact portion is configured or adapted to contact a patient's forehead. Further, the contact portion includes a contact portion shell formed as an outer wall, which defines a single, continuous inner cavity. The contact portion shell is formed from a substantially deformable material, such that the wall of the contact portion shell is deformable and deflectable upon contact with the patient's forehead. In addition, the continuous inner cavity does not include any support structure, such as support ribs, retaining walls, support members, etc., positioned within the cavity.

The present invention is further directed to a forehead support assembly having a forehead support member and a forehead pad. The forehead pad includes a coupling portion and a contact portion. The coupling portion is attachable to the forehead support member, and the contact portion contacts a patient's forehead. The contact portion includes a contact portion shell formed as an outer wall, which defines a single, continuous inner cavity. The contact portion shell is formed from a substantially deformable material, such that the wall of the contact portion shell is deformable and deflectable upon contact with the patient's forehead. The continuous inner cavity does not include any support structure positioned within or extending within the cavity.

These and other features and characteristics of the present invention, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and the claims, the singular form of "a", "an", and "the" include plural referents unless the context clearly dictates otherwise.

DETAILED DESCRIPTION OF THE EXEMPLARY EMBODIMENTS

Figure 1:
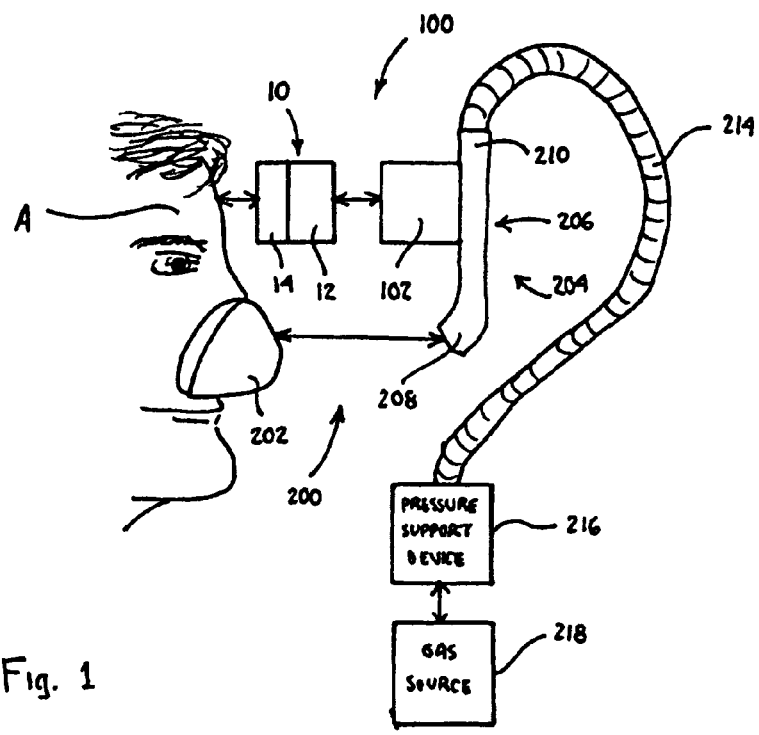
FIG. 1 is a schematic view of a forehead pad and a forehead support assembly according to the principles of the present invention for use in connection with a patient interface device.

The present invention is directed to a forehead pad 10 and forehead support assembly 100 as illustrated in various embodiments in FIGS. 1-13. In particular, and as illustrated in FIGS. 1 and 11-13, the forehead pad 10 and forehead support assembly 100 are designed to be used in connection with a patient interface device 200, which includes a mask 202 and a mask attachment assembly (not shown). The mask can be a nasal mask, a nasal and oral mask, a full-face mask, nasal cannula, and similar masks and structures as are known in the art that provide a sealed communication with an airway of a patient. Also as known in the art, mask 202 allows gas, such as oxygen, air and the like, to flow through and into the mask for inhalation by the patient or user.

Forehead support assembly 100 is designed to be used in connection with mask 202 for providing support or contact with a user's forehead A. In particular, forehead support assembly 100 includes a forehead support member 102. Further, the forehead support assembly 100 includes forehead pad 10 and forehead support member 102.

Forehead pad 10 and forehead support assembly 100 of the present invention can be used in connection with a variety of masks 202. For example, as shown in schematic form in FIG.

1, the forehead support member 102 may be connectable to a connection assembly 204, which is in operative communication with a mask conduit coupling 206. The mask conduit coupling is, in turn, in fluid communication with mask 202. In this embodiment, forehead support member 102 is directly or indirectly in contact with connection assembly 204, as well as mask conduit coupling 206. However, it is also envisioned that forehead support assembly 100 of the present invention is connected, whether directly or indirectly, with mask 202, as show, for example, in FIGS. 11-13.

In one embodiment, forehead support assembly 100 and forehead pad 10 of the present invention are used in connection with the above-discussed mask conduit coupling 206. The mask conduit coupling is in fluid communication with mask 202 via a mask port (not shown). In a further embodiment, mask conduit coupling 206 includes a first end 208 and a second end 210. The first end of the mask conduit coupling is attached to mask 202. The second end of the mask conduit coupling is in fluid communication with a patient circuit 214, a pressure support device 216, a gas source 218, or any combination thereof.

Referring now to FIGS. 1-10, an exemplary embodiment of forehead pad 10 (FIGS. 1-8) and forehead support assembly 100 (FIGS. 9 and 10) will be described. Forehead pad 10 includes a coupling portion 12, which includes a structure or mechanism for attachment to forehead support member 102 in forehead support assembly 100. In addition, forehead pad 10 includes a contact portion 14. Contact portion 14 is adapted or configured to contact the patient's or user's forehead A, and is formed as a contact portion shell 16. Further, the contact portion shell 16 is formed as an outer wall 18 that defines a single, continuous inner cavity 20 in the entirety of the forehead pad. Still further, contact portion shell 16 is formed from a substantially deformable material, such that wall 18 of the contact portion shell is deformable and deflectable upon contact with the patient's forehead A.

Figure 2:
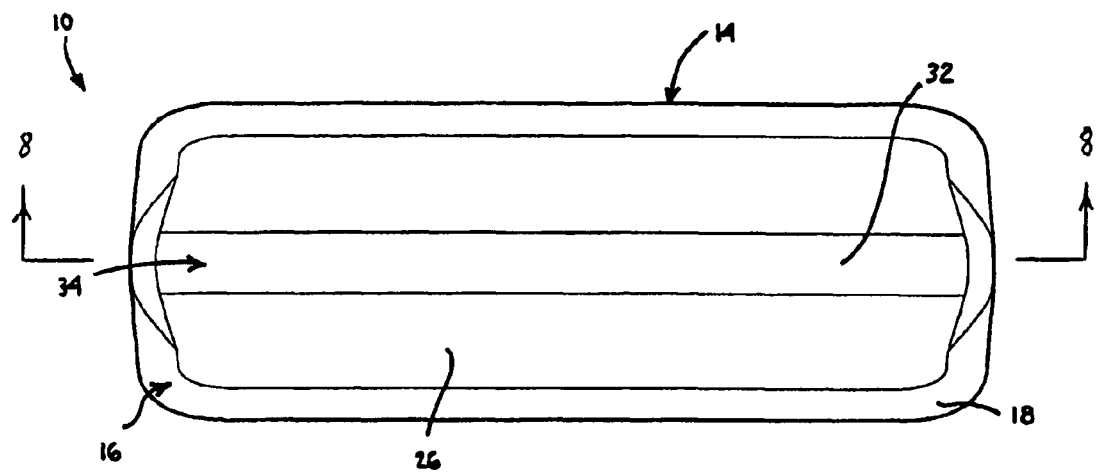
FIG. 2 is a front view of one embodiment of a forehead pad according to the principles of the present invention.
Figure 3:
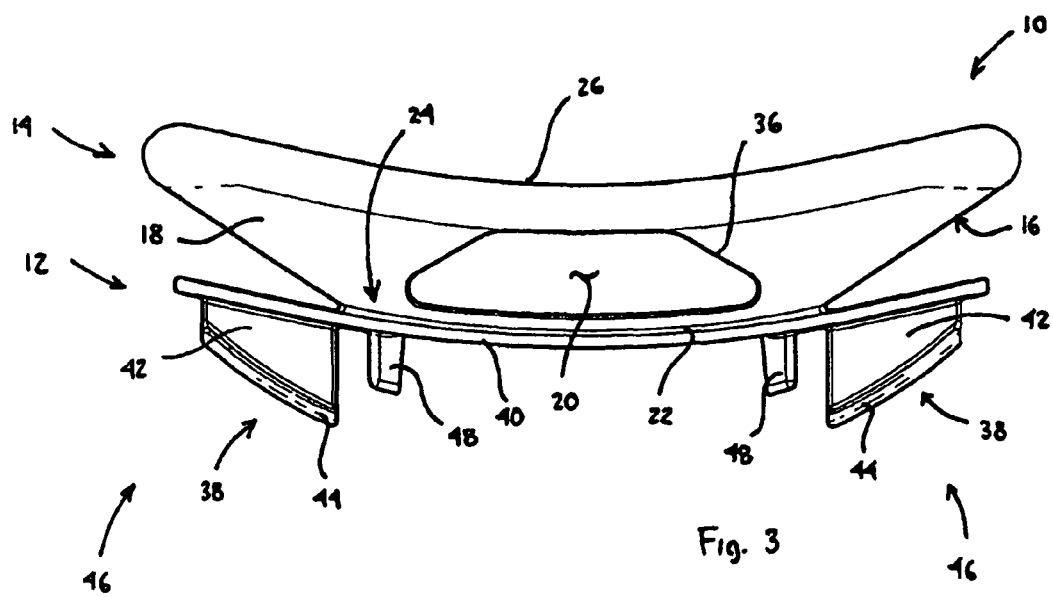
FIG. 3 is a top view of the forehead pad of FIG. 2.

Unlike prior art structures, contact portion shell 16 of the present invention does not include any support structure disposed or extending within cavity 20. For example, as seen in FIGS. 2 and 3 of the '556 patent, retaining walls 28 and 30 are formed as inner walls extending through the inner cavity, and these walls 28 and 30 are specifically used to provide structural integrity to the forehead contact support pads. However, contact portion shell 16 of the present invention, and, in particular, wall 18 of the contact portion shell, is formed from a substantially deformable material that is structural, and does not require any supporting structure. Instead, contact portion shell 16 is manufactured from a material that, when deformed, even for long periods of time, returns to its original shape when the deforming forces are removed.

Further, because there are no supporting members or structure within inner cavity 20, forehead pad 10 provides a continuously deformable and deflectable shell 16 that is capable of conforming quite well to the contours of the user's forehead A. Accordingly, little or no pressure points are evident when the patient is using forehead pad 10 according to the principles of the present invention. As a result, forehead pad 10 and forehead support assembly 100 of the present invention are much more comfortable than the conventional forehead pads and assemblies.

Figure 7:
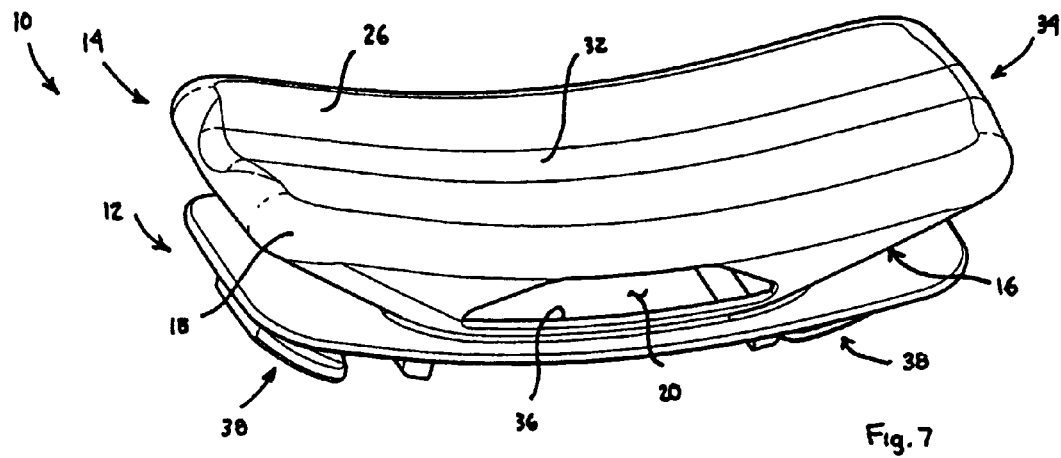
FIG. 7 is a front perspective view of the forehead pad of FIG. 2.

In order to achieve these beneficial deformation and deflection characteristics, the present invention contemplates that the substantially deformable material of contact portion shell 16 is silicone, a silicone-based material, a low-durometer silicone, an elastomeric material, a soft elastomer, a thermoplastic elastomer, or any combination thereof. In addition, in order to provide greater convenience and comfort to the user, and as best illustrated in FIGS. 3 and 7 of the present application, contact portion 14 of forehead pad 10 may have a substantially concave shape. This concave shape contacts the patient's forehead A and conforms upon the contours of the patient's forehead A.

As one of the benefits and goals of the present invention is to provide a new and improved contact structure and pad for use in connection with a forehead support assembly, there are other manners of adjusting the deformation and deflection characteristics of the forehead pad 10. For example, the deformation and deflection characteristics of contact portion 14 of forehead pad 10 may be modified by providing a variable wall 18 thickness. In particular, the wall thickness of varying portions of contact portion shell 16 can be modified to provide greater or lesser deformation, and, therefore, pressure points, on the user's forehead A in use.

The deformation and deflection characteristics of contact portion shell 16 can also be modified through the use of a living hinge 22. For example, the living hinge 22 can be formed on a portion at a root 24 of contact portion 12. Accordingly, any deformation or deflection of contact portion 14 would begin at living hinge 22 at root 24 of contact portion shell 16. Still further, the use of this living hinge also provides a more uniform movement of contact portion 14 when used in connection with the user's forehead A. For example, if the user pressed or moved the contact portion 14 in place against the user's forehead A, as opposed to crumpling or otherwise creasing upon deflection or deformation, living hinge 22 would allow the entire surface of the contact portion 14 to move in a uniform manner to better mate with the surface of the user. This provides additional convenience and comfort characteristics.

Wall 18 of contact portion shell 16 also includes a contact surface 26 that directly contacts the patient's forehead A. In order to provide additional comfort, at least a portion of contact surface 26 of contact portion 14 may include a textured surface 28. See FIGS. 11 and 13. In addition, contact surface 26 may provide some desirous feel to the patient's forehead A through the use of this textured surface, or the use of some coating layer or any combination thereof, for modifying the feeling of the contact surface when contacting the patient's forehead A. Of course, it is also envisioned that forehead pad 10, and, specifically, contact portion 14, can be manufactured from a material that provides this desirous effect. For example, contact portion 14 and/or contact surface 26 can be made from a silicone or silicone-based material that provides the user with a "slippery" feeling in use, which lends itself to additional comfort and other beneficial characteristics. Of course, as discussed above, such a feel could also be provided through the use of a coating layer or other textured surface.

Figure 11:
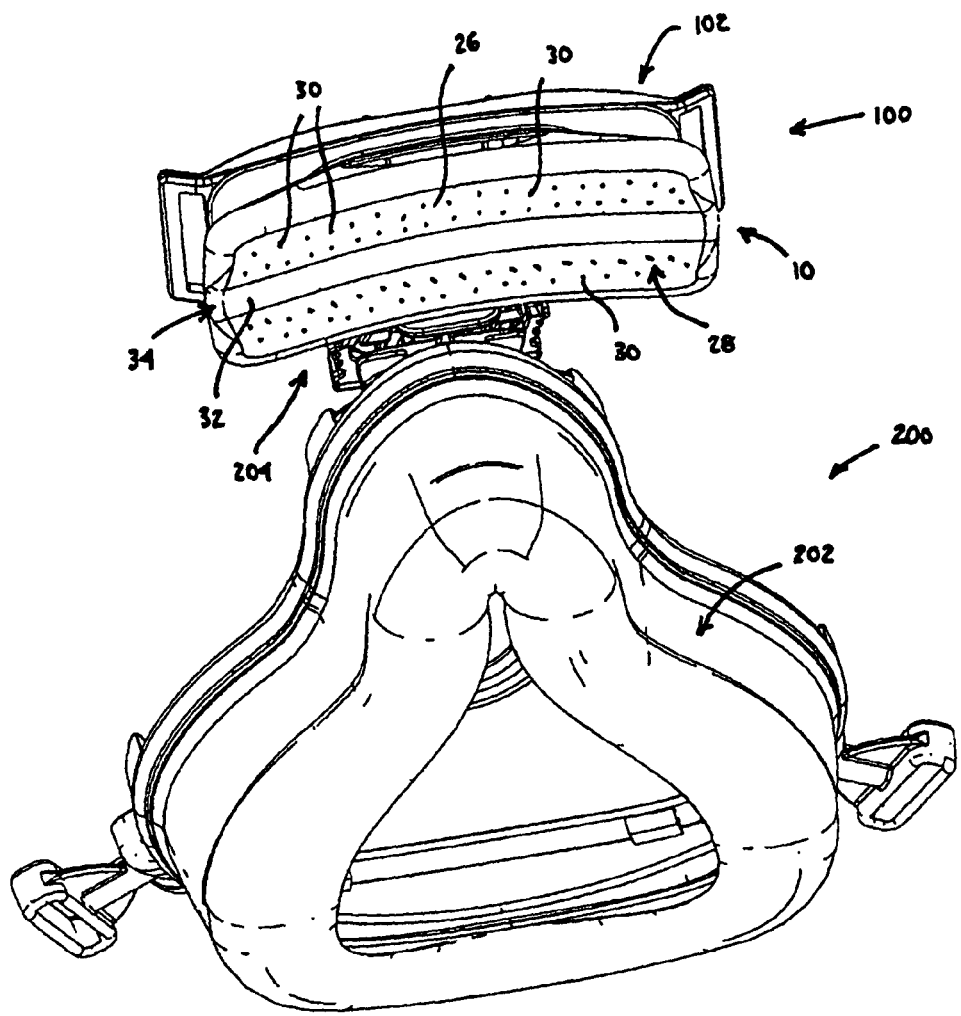
FIG. 11 is a rear perspective view of a forehead support assembly coupled to a mask.
Figure 12:
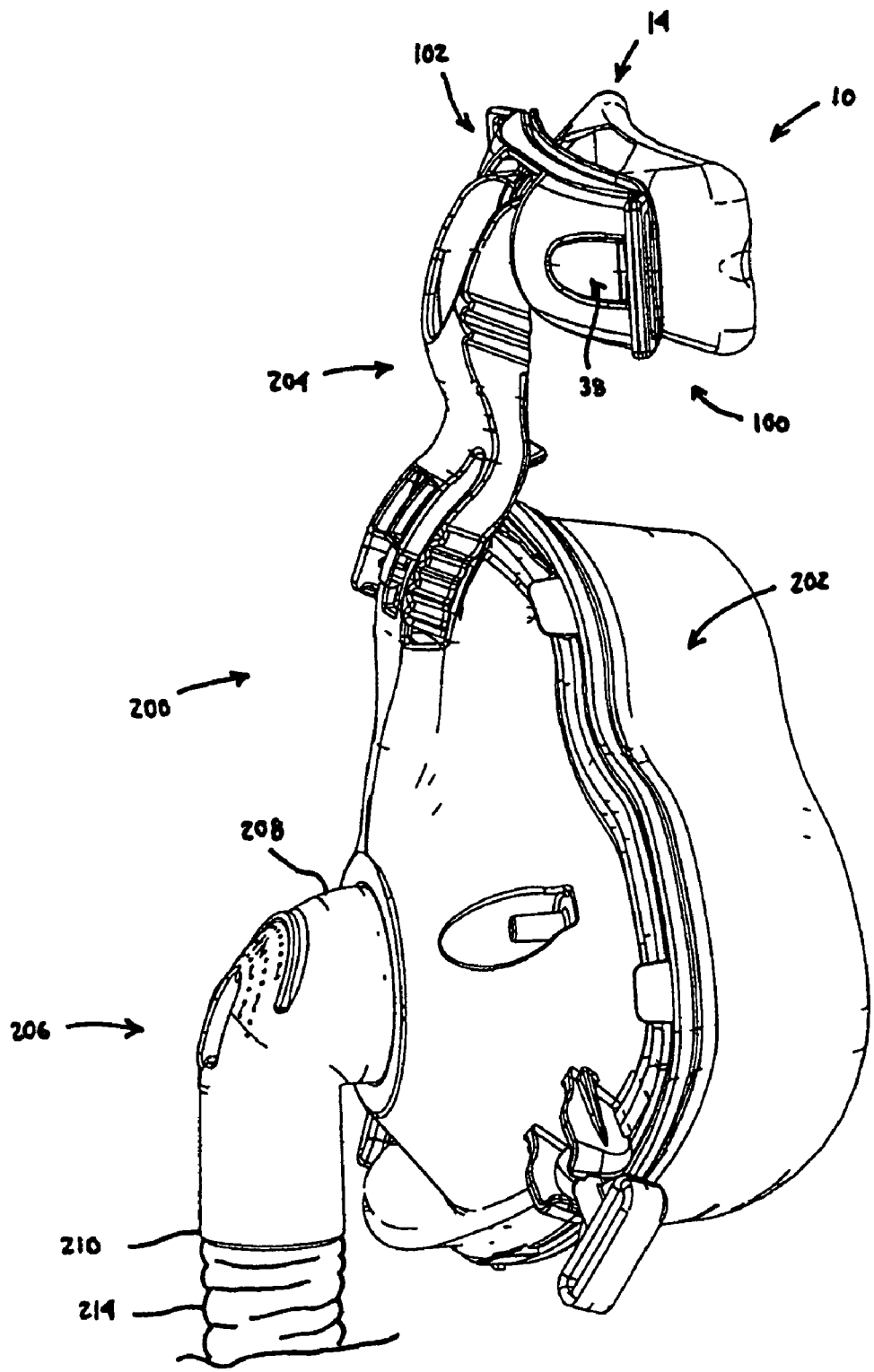
FIG. 12 is a front perspective view of the forehead support assembly and mask of FIG. 11.
Figure 13:
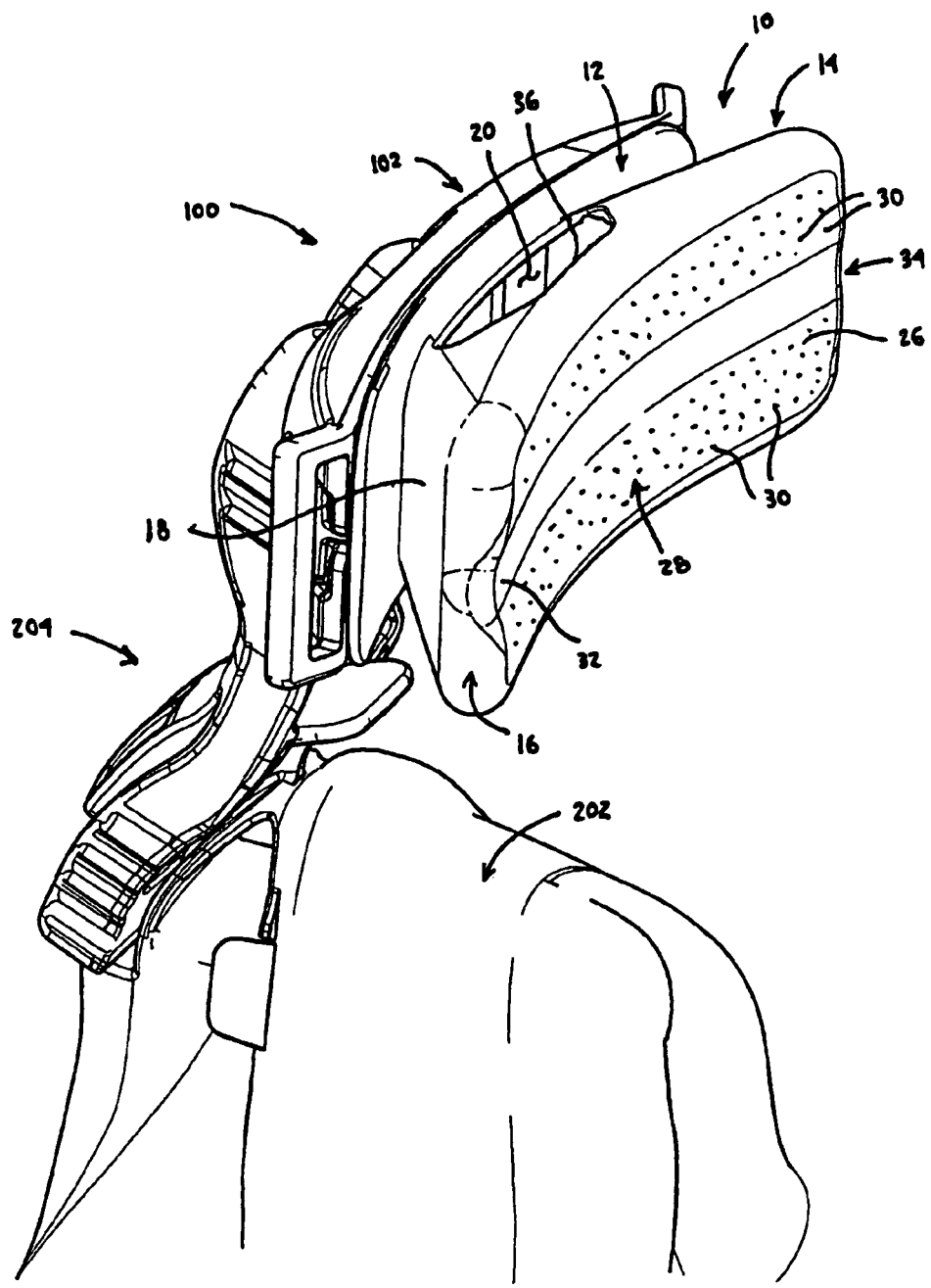
FIG. 13 is a still further rear perspective view of the forehead support assembly and mask of FIG. 11.

Textured surface 28 may be a series of projections, bumps, ridges, orifices or other similar textures formed on contact surface 26 of contact portion 14. Again, as best seen in FIGS. 11 and 13, contact surface 26 may include at least one orifice 30 extending through wall 18 of contact portion shell 16 and into inner cavity 20. In one embodiment, contact surface 26 includes a plurality of orifices 30 spaced about and extending through wall 18 of contact portion shell 16. Not only can such a textured surface provide additional comfort to the patient's forehead A, it also allows the air to better circulate over the surface of the patient under the forehead pad when the patient is using the forehead pad. In addition, the use of orifices 30 prevent a vacuum seal from occurring between contact portion 14 and the user's forehead A, which is obviously an undesirable condition.

Figure 8:
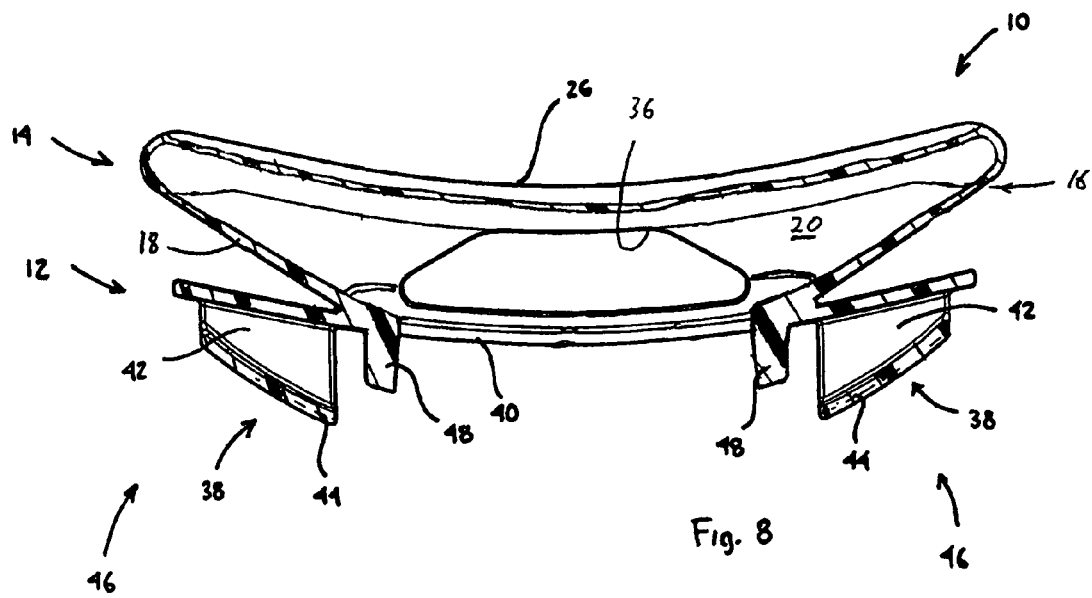
FIG. 8 is a cross-sectional view of the forehead pad taken along line 8-8 of FIG. 2.

In a further embodiment, contact surface 26 includes a groove 32 that extends along a portion of the contact surface. In one embodiment, and as best seen in FIGS. 2, 7, and 8, groove 32 extends across a central portion 34 of the contact surface 26. As discussed above in connection with the orifices 30, groove 32 provides additional comfort when the forehead pad is used in connection with the user's forehead A, for example by preventing an undesirable seal between the user's forehead A and contact surface 26.

Figure 6:
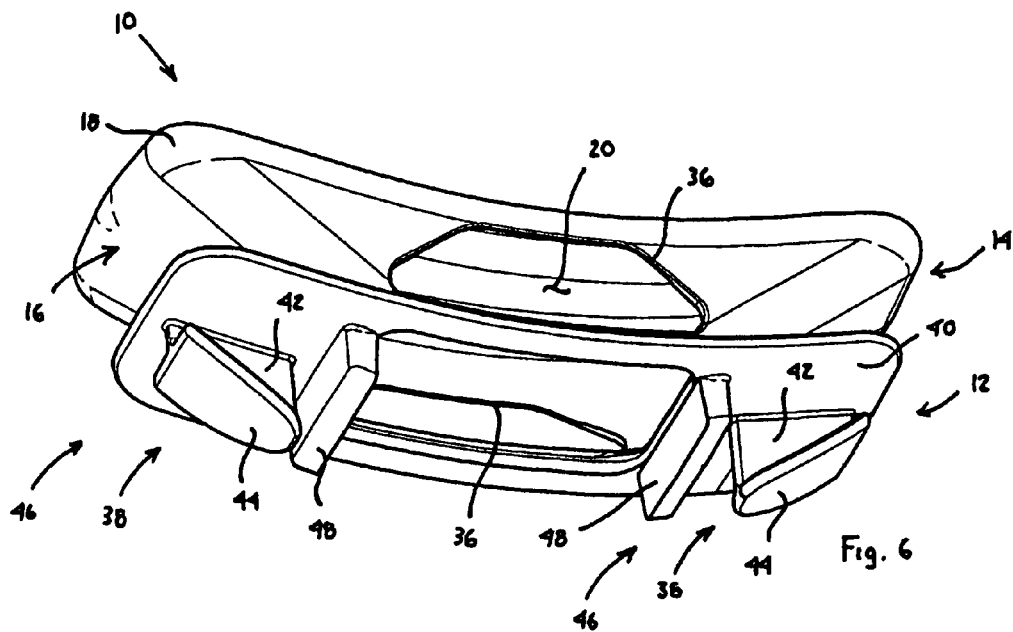
FIG. 6 is a rear perspective view of the forehead pad of FIG. 2.

As seen in FIGS. 3, 6, and 7, and in one embodiment of the present invention, contact portion shell 16 also includes one or more cutouts 36 that extend through wall 18 of contact portion shell 16 and into inner cavity 20. Cutouts 36 achieve two functions. First, when used in connection with orifices 30, they allow for better circulation of air into orifices 30, because air can pass into inner cavity 20 through the cutouts 36. In addition, the cutouts modify the deformation and deflection characteristics of contact portion shell 16. Still further, cutouts 36 allow contact portion shell 16 to more easily yield when placed against the user's forehead A. For example, if the cutouts were not present, it would be much more difficult for air to escape inner cavity 20, which would result in a much more rigid and unyielding structure.

Figure 4:
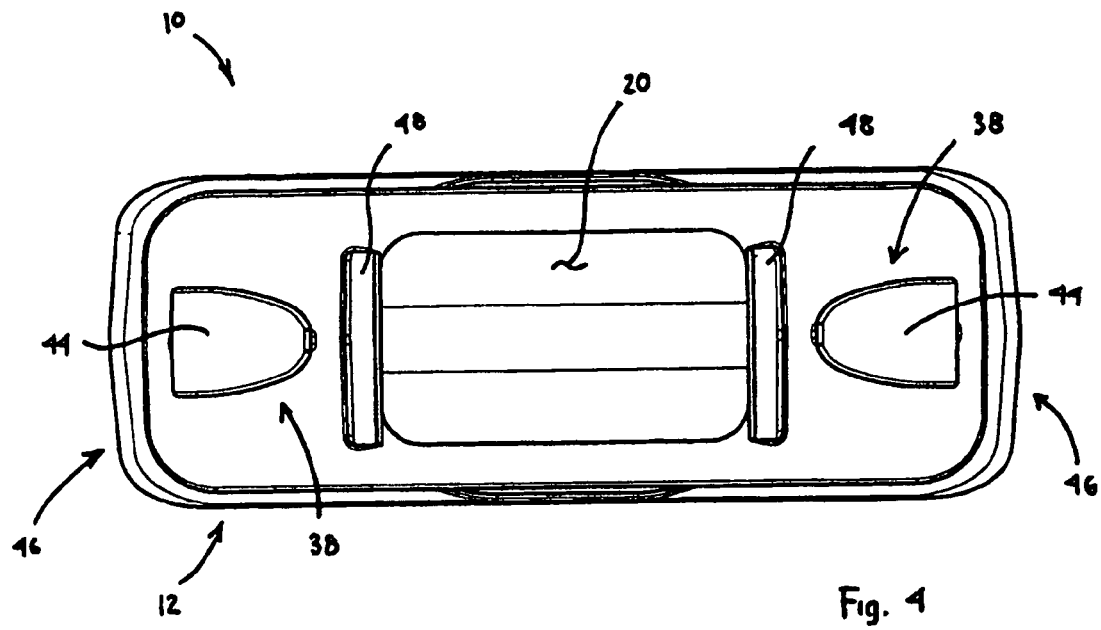
FIG. 4 is a rear view of the forehead pad of FIG. 2.
Figure 5:
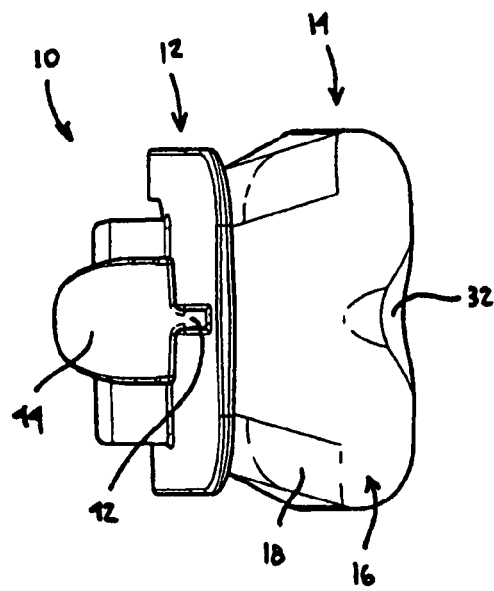
FIG. 5 is side view of the forehead pad of FIG. 2.
Figure 9:
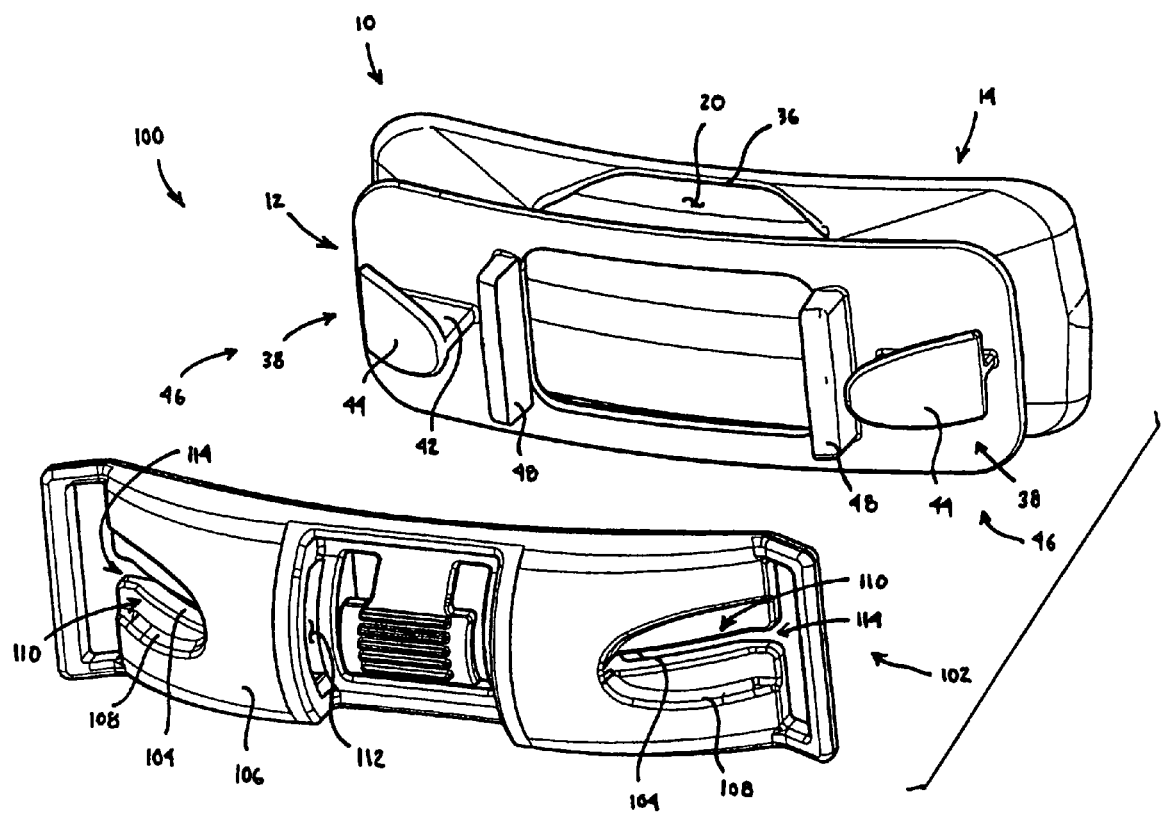
FIG. 9 is a rear perspective, exploded view of a forehead pad and a forehead support member upon which the forehead pad is connectable according to the principles of the present invention.
Figure 10:
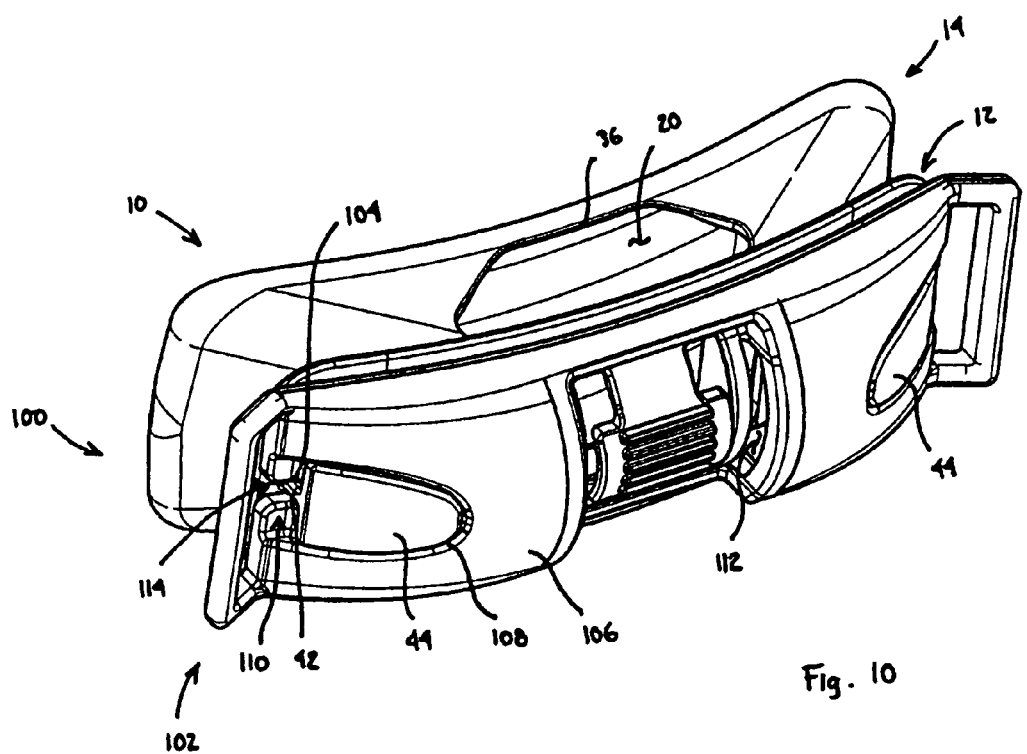
FIG. 10 is a rear perspective view of the forehead pad of FIG. 8 connected to the forehead support member of FIG. 8.

As seen in FIGS. 3, 4, and 6, and as seen in connection with a forehead support member 102 in FIGS. 9 and 10, coupling portion 12 may include one or more connection tabs 38. In the illustrated exemplary embodiment, connection tabs 38 extend from a coupling portion wall 40 and are adapted, sized, or configured to engage a mating slot 104 on the forehead support member 102. In use, coupling portion 12 is attached by inserting connection tabs 38 through slot 104, such that coupling portion 12, and, thereby, contact portion 14, is attached to forehead support member 102. In this manner, forehead support member 102 is attached to or otherwise in operable engagement with or part of forehead support assembly 100 for use in connection with mask 202.

As seen in a disengaged arrangement (FIG. 9) and an engaged arrangement (FIG. 10), coupling portion 12 of forehead pad 10 may include multiple connection tabs 38. As also seen in this embodiment, the connection tab 38 includes a neck 42 and a contact surface 44. Neck 42 is engageable with slot 104 of the forehead support member 102, while contact surface 44 of connection tab 38 contacts a forehead support member wall 106. In this manner, the coupling portion 12 is connected to forehead support member 102.

In another embodiment, forehead support member 102 includes a rim 108 projecting from or recessed within forehead support member wall 106 and forming a seat 110 on forehead support member 102. Seat 110 allows for the beneficial contact of contact surface 44 of connection tab 38, which further secures connection tab 38, and, therefore, coupling portion 12, to forehead support member 102. It is envisioned that seat 110 can be recessed within forehead support member wall 106, or, alternatively, rim 108 can extend beyond the surface of the forehead support member wall. In a further embodiment, forehead support member 102 includes an inner cavity 112, and a portion of rim 108 and/or seat 110 extends into inner cavity 112.

In one embodiment, coupling portion 12 includes a coupling mechanism 46 for attaching coupling portion 12 to forehead support member 102. In addition, coupling mechanism 46 can provide for the removable attachment of coupling portion 12 to forehead support member 102, such that forehead pad 10 is removable from the forehead support member. This would allow for the replacement of forehead pad 10 for maintenance or other purposes. Of course, coupling mechanism 46 can be the above-discussed connection tabs 38 and rim 108/seat 110 arrangement.

Further, in another embodiment, coupling portion 12 includes an extension member 48 extending from coupling portion wall 40. In one preferred embodiment, there are multiple extension members 48 extending from coupling portion wall 40. In the illustrated exemplary embodiment, extension members 48 are positioned adjacent and spaced from connection tabs 38. In operation, when neck 42 and contact surface 44 of connection tabs 38 are inserted through slot 104 of forehead support member 102, the extension member abuts rim 108 and/or seat 110 in inner cavity 112 of forehead support member 102. Such an arrangement not only provides better engagement of coupling portion 12 to forehead support member 102, but it also lends greater structural integrity to coupling portion 12, contact portion 14, and forehead pad 10, generally.

In addition, and in another embodiment, as best seen in FIG. 3, contact surface 44 of connection tab 38 is contoured or slanted in order to effectively mate with and seat within rim 108 and seat 110 of forehead support member 102. This slant or contour of contact surface 44 is used in connection with a specifically designed forehead support member 102 that has a generally convex shape. In any case, when connection tabs 38 and extension members 48 are used as the coupling mechanism 46, they should be appropriately sized and shaped so as to properly engage forehead support member 102.

In a still further embodiment, and as best seen in FIGS. 9 and 10, slot 104 of forehead support member 102 includes a tapered slot entry 114. Tapered slot entry 114 facilitates easier engagement of neck 42 and contact surface 44 of connection tabs 38 within slot 104. In particular, tapered slot entry 114 allows for easier location of neck 42 and contact surface 44, and also facilitates faster engagement with the slot in the forehead support member.

In order to effect the removal of connection tabs 38 from slots 104 of forehead support member 102, the connection tab can also be formed from a deformable material. In this manner, the user may bend, move, rotate, or otherwise manipulate connection tab 38, and, specifically, neck 42 and contact surface 44 of the connection tab, into and out of an engaging relationship with the slot 104. Once in place, connection tab 38 will regain its structural alignment and properly engage in seat 110 and rim 108 of forehead support member 102. Such an arrangement allows for the easy removal, yet secure attachment, of forehead pad 10 to forehead support member 102.

While it has been discussed above that contact portion 14 is manufactured or formed from a deformable and deflectable material, it is further envisioned that coupling portion 12 is manufactured from the same material. In this manner, coupling portion 12 and contact portion 14 may be integrally formed from the same material during a molding process. This allows for the easy manufacture of the forehead pad of the present invention.

It is also envisioned that multiple forehead pads 10 can be used in connection with the same forehead support member 102. As discussed above in connection with forehead pad 10, the use of multiple forehead pads 10 utilize the same deformable and deflectable material in order to achieve similar and beneficial deformation and deflection characteristics.

In this manner, forehead pad 10 and forehead support assembly 100 of the present invention can be used in connection with a patient interface device 200 and/or mask 202 and provide the user with a more comfortable contact, specifically with reference to the user's forehead A. In addition, forehead pad 10 and forehead support assembly 100 of the present invention reduces and/or eliminates various pressure points that are associated with conventional forehead pads and assemblies.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A forehead pad, comprising:
   (a) a coupling portion; and
   (b) a contact portion comprising:
      (1) a patient contacting surface having a generally rectangular and concave shape in a non-deflected state, the patient contacting surface having a longitudinal axis extending from a first end of the contact portion to a second end of the contact portion opposite the first end of the contact portion, and wherein the patient contacting surface is configured to contact a patient's forehead such that the concave shape faces such a patient's forehead responsive to the forehead pad being placed against such a patient, and
      (2) four side walls, each of which is integral with the patient contacting surface such that one side wall extends from each side of the patient contacting surface, wherein the four side walls and the patient contacting surface define a single, continuous inner cavity, wherein the contact portion is formed from a substantially deformable material such that the four side walls are deformable and deflectable upon contact with the patient's forehead, wherein the continuous inner cavity does not include any support structure therein, wherein the four side walls include a first side wall provided at the first end of the contact portion and a second side wall provided at the second end of the contact portion, wherein the first side wall and the second side wall are closed and generally perpendicular to the longitudinal axis of the patient contacting surface, wherein the four side walls further include a third side wall and a fourth side wall each being generally parallel to the longitudinal axis of the patient contacting surface and extending from the first side wall to the second side wall and downwardly from the patient contacting surface, wherein an orifice is defined generally at a central location in each of the third side wall and the fourth side wall such that the third side wall and the fourth side wall each include an open central portion and first and second closed end portions provided adjacent the open central portion on opposite sides of the open central portion, and wherein each orifice extends into the inner cavity to allow a central portion of the forehead pad to deform more readily than other portions of the forehead pad responsive to a force being applied to the patient contacting surface.

2. The forehead pad of claim 1, wherein the substantially deformable material is silicone, a silicone-based material, a low-durometer silicone, an elastomeric material, a soft elastomer, a thermoplastic elastomer, or any combination of two or more of silicone, a silicone-based material, a low-durometer silicone, an elastomeric material, a soft elastomer, and a thermoplastic elastomer.

3. The forehead pad of claim 1, wherein each side wall includes edge portions generally proximal a corner of the patient contacting surface, and wherein the edge portions of adjacent side walls are integral with one another.

4. The forehead pad of claim 1, wherein deformation and deflection characteristics of the contact portion are modified by providing at least a portion of a least one of the four side walls with a variable wall thickness.

5. The forehead pad of claim 1, wherein a living hinge is formed at least a portion of a root of the contact portion, such that any deformation and deflection of the contact portion will initiate at the living hinge at the root.

6. The forehead pad of claim 1, wherein at least a portion of the patient contacting surface includes a textured surface, a coating layer, or any combination thereof.

7. The forehead pad of claim 1, wherein the patient contacting surface provides a tactile feel to the patient's forehead through the material, a textured surface, a coating layer, or any combination thereof.

8. The forehead pad of claim 1, wherein the patient contacting surface includes a plurality of orifices spaced about and extending therethrough and into the inner cavity.

9. The forehead pad of claim 1, wherein the patient contacting surface includes a groove extending along at least a portion thereof.

10. The forehead pad of claim 1, wherein the coupling portion includes at least one connection tab extending from a coupling portion wall and configured to engage a mating slot on a forehead support member, such that the coupling portion, and thereby the contact portion, is attachable to such a forehead support member.

11. The forehead pad of claim 1, wherein the coupling portion includes a coupling mechanism for attaching the coupling portion to a forehead support member, wherein the coupling mechanism provides for the removable attachment of the coupling portion to such a forehead support member.

12. The forehead pad of claim 1, wherein the coupling portion and the contact portion are integrally formed from the same substantially deformable material in a molding process.

13. A forehead support assembly, comprising:
   (a) a forehead support member; and
   (b) a forehead pad, including:
      (1) a coupling portion, and
      (2) a contact portion comprising:
         (i) a patient contacting surface having a generally rectangular and concave shape in a non-deflected state, the patient contacting surface having a longitudinal axis extending from a first end of the contact portion to a second end of the contact portion opposite the first end of the contact portion, and wherein the patient contacting surface is configured to contact a patient's forehead such that the concave shape faces such a patient's forehead responsive to the forehead pad being placed against such a patient, and
         (ii) four side walls, each of which is integral with the patient contacting surface such that one side wall extends from each side of the patient contacting surface, wherein the four side walls and the patient contacting surface define a single, continuous inner cavity, wherein the contact portion is formed from a substantially deformable material, such that the four side walls are deformable and deflectable upon contact with the patient's forehead, wherein the continuous inner cavity does not include any support structure therein, wherein the four side walls include a first side wall provided at the first end of the contact portion and a second side wall provided at the second end of the contact portion, wherein the first side wall and the second side wall are closed and generally perpendicular to the longitudinal axis of the patient contacting surface, wherein the four side walls further include a third side wall and a fourth side wall each being generally parallel to the longitudinal axis of the patient contacting surface and extending from the first side wall to the second side wall and downwardly from the patient contacting surface, wherein an orifice is defined generally at a central location in each of the third side wall and the fourth side wall such that the third side wall and the fourth side wall each include an open central portion and first and second closed end portions provided adjacent the open central portion on opposite sides of the open central portion, and wherein each orifice extends into the inner cavity to allow a central portion of the forehead pad to deform more readily than other portions of the forehead pad responsive to a force being applied to the patient contacting surface.

14. The forehead support assembly of claim 13, wherein the coupling portion of the forehead pad includes at least one connection tab extending from a coupling portion wall and configured to engage a mating slot positioned on the forehead support member, such that the coupling portion, and thereby the contact portion, is attachable to the forehead support member.

15. The forehead support assembly of claim 14, wherein the connection tab includes a neck and a contact surface, wherein the neck is engageable with the slot of the forehead support member and the contact surface of the connection tab contacts a forehead support member wall, thereby engaging the coupling portion with the forehead support member.

16. The forehead support assembly of claim 15, wherein the forehead support member includes a rim forming a seat for the contact surface of the connection tab, thereby further securing the connection tab, and therefore the coupling portion of the forehead pad, to the forehead support member.

17. The forehead support assembly of claim 13, wherein the forehead support member is connectable to a connection assembly in operative communication with a mask conduit coupling, a mask or any combination thereof.

* * * * *